US008021517B2

(12) United States Patent
Hughes et al.

(10) Patent No.: US 8,021,517 B2
(45) Date of Patent: Sep. 20, 2011

(54) USE OF FLUORESCENT NANOPARTICLES TO MAKE ON-LINE MEASUREMENTS OF CROSS-WEB AND MACHINE-DIRECTION COMPONENT AND PROPERTY VARIATIONS IN PAPER AND CONTINUOUS WEB PRODUCTS

(75) Inventors: Michael Kon Yew Hughes, Vancouver (CA); Sebastien Tixier, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 864 days.

(21) Appl. No.: 12/039,696

(22) Filed: Feb. 28, 2008

(65) Prior Publication Data
US 2009/0218060 A1 Sep. 3, 2009

(51) Int. Cl.
*D21H 11/00* (2006.01)

(52) U.S. Cl. ............. 162/175; 162/162; 162/181.1; 162/183; 250/458.1; 250/459.1; 250/461.1; 250/461.2

(58) Field of Classification Search ............. 162/175; 250/459.1
See application file for complete search history.

(56) References Cited

U.S. PATENT DOCUMENTS

| 4,239,593 | A | 12/1980 | Dunsmoor, Jr. |
|---|---|---|---|
| 4,376,012 | A | 3/1983 | Bergstrom |
| 4,577,337 | A | 3/1986 | Light |
| 4,783,314 | A | 11/1988 | Hoots et al. |
| 4,879,471 | A | 11/1989 | Dahlquist |
| 4,943,721 | A | 7/1990 | Vidrine, Jr. |
| 5,094,535 | A | 3/1992 | Dahlquist et al. |
| 5,315,124 | A | 5/1994 | Goss et al. |
| 5,432,353 | A | 7/1995 | Goss et al. |
| 5,795,394 | A | 8/1998 | Belotserkovsky et al. |
| 5,854,821 | A | 12/1998 | Chase et al. |
| 5,900,113 | A | 5/1999 | Tubergen |
| 6,074,483 | A | 6/2000 | Belotserkovsky et al. |
| 6,086,716 | A | 7/2000 | Watson et al. |
| 6,092,003 | A | 7/2000 | Hagart-Alexander et al. |
| 6,410,926 | B1 | 6/2002 | Munro et al. |
| 6,466,839 | B1 | 10/2002 | Heaven et al. |
| 6,649,138 | B2 | 11/2003 | Adams et al. |
| 6,682,810 | B1 | 1/2004 | Jones et al. |
| 6,783,699 | B2 | 8/2004 | Li et al. |

(Continued)

OTHER PUBLICATIONS

Yu-Jen Shen & Yuh-Lang Lee, Assembly of CdS quantum dots onto mesoscopic TiO2 films for quantum dot-sensitized solar cell applications, Nanotechnology Jan. 4, 2006 pp. 1-7 vol. 19.

(Continued)

*Primary Examiner* — Eric Hug
*Assistant Examiner* — Jacob Thomas Minskey
(74) *Attorney, Agent, or Firm* — Cascio Schmoyer & Ziervas

(57) ABSTRACT

Fluorescent nanoparticles such as quantum dots are incorporated into paper and other web products such as plastics to achieve cross-direction and machine direction on-line detection of selected components during manufacture. Fluorescent nanoparticles markers are added in known proportions into product formulations along with the selected components of interest. By detecting the fluorescence from the nanoparticles, the selected components can be traced at various stages of production. In addition, by using different fluorescent nanoparticles that emit radiation at different wavelengths, data from individual materials or layers in a composite structure can be ascertained simultaneously with a single sensor. The technique is particularly suited for monitoring expensive and difficult-to-measure components that may be present only in trace quantities. The technique can be implemented continuously during normal production, during start-up or re-formulation, such as a grade change in paper production, when considerable changes in the process parameters occur.

20 Claims, 1 Drawing Sheet

U.S. PATENT DOCUMENTS

| | | |
|---|---|---|
| 6,872,450 B2 | 3/2005 | Liu et al. |
| 6,985,221 B2 | 1/2006 | Semersky et al. |
| 7,081,489 B2 | 7/2006 | Chen et al. |
| 7,192,780 B2 | 3/2007 | Liu et al. |
| 7,255,918 B2 | 8/2007 | Watanabe et al. |
| 2007/0119561 A1 | 5/2007 | Doelle et al. |
| 2007/0258316 A1 | 11/2007 | Matula |
| 2008/0041542 A1* | 2/2008 | Gray et al. .................... 162/102 |
| 2008/0064113 A1* | 3/2008 | Goix et al. ...................... 436/86 |

OTHER PUBLICATIONS

J C Grunlan et al. High-throughput measurement of polymer film thickness using optical dyes, Meas.Sci.Technol. 2005 pp. 153-161 vol. 16.

JM Corres et al. Design of pH Sensors in Long-Period Fiber Gratings Using Polymeric Nanocoatings IEEE Sensors Journal, Mar. 2007 pp. 455-463, vol. 7 No. 3.

* cited by examiner

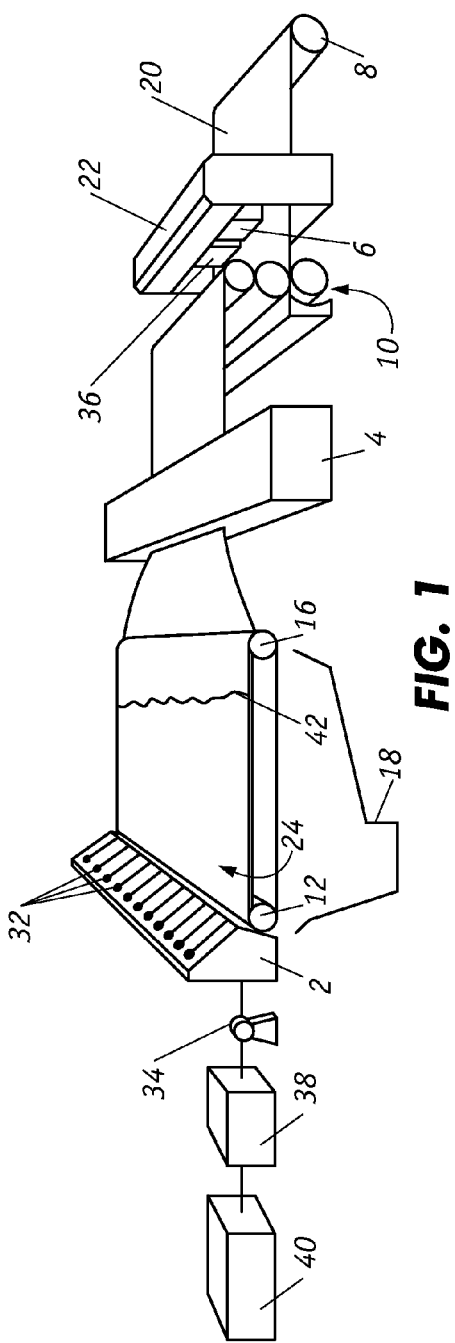
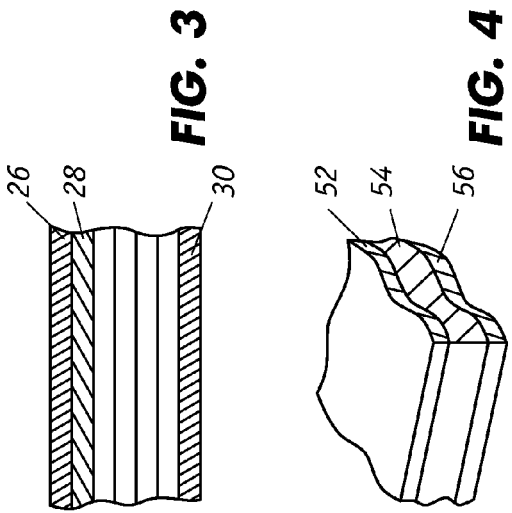
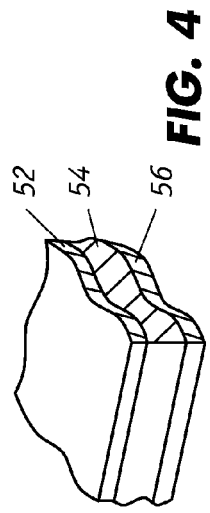
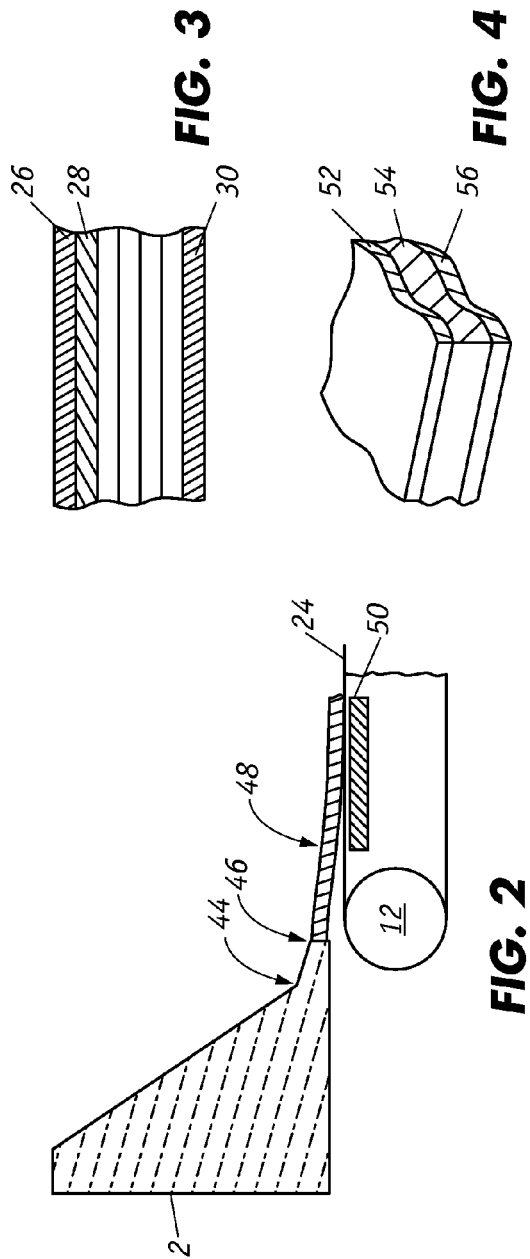
FIG. 1
FIG. 2
FIG. 3
FIG. 4

USE OF FLUORESCENT NANOPARTICLES TO MAKE ON-LINE MEASUREMENTS OF CROSS-WEB AND MACHINE-DIRECTION COMPONENT AND PROPERTY VARIATIONS IN PAPER AND CONTINUOUS WEB PRODUCTS

The present invention generally relate to the employment of fluorescent nanoparticles such as quantum dots to detect the presence of specific components in paper and other sheet products. In particular, in the case of paper products, known amounts of fluorescent nanoparticles are added to the wet stock along with the specific components of interest and detection of fluorescence that is emitted from the paper yields information regarding the amounts of the specific components present.

BACKGROUND OF THE INVENTION

In the manufacture of paper on continuous papermaking machines, a web of paper is formed from an aqueous suspension of fibers (stock) on a traveling mesh wire or fabric and water drains by gravity and vacuum suction through the fabric. The web is then transferred to the pressing section where more water is removed by dry felt and pressure. The web next enters the dryer section where steam heated dryers and hot air completes the drying process. The papermaking machine is essentially a de-watering, i.e., water removal, system. In the sheetmaking art, the term machine direction (MD) refers to the direction that the sheet material travels during the manufacturing process, while the term cross direction (CD) refers to the direction across the width of the sheet which is perpendicular to the machine direction.

A wide range of chemicals is utilized in the papermaking stock furnish to impart or enhance specific sheet properties or to serve other necessary purposes. Such additives as alum, sizing agents, mineral fillers, starches and dyes are commonly used. Chemicals for control purposes such as drainage aids, defoamers, retention aids, pitch dispersants, slimicides, and corrosion inhibitors are added as required. Fabrication of quality paper requires addition of the proper amounts of these chemicals.

Many of the additives are removed in de-watering process; however, others such as ash remain in the final paper product. Generally speaking, ash is defined as the residue remaining after complete combustion of paper. Ash can include various materials. Many paper manufacturers use clay, titanium dioxide ($TiO_2$) or calcium carbonate ($CaCO_3$); and in some cases barium sulfate and talc also comprise ash. In some cases only one of these materials will be used, whereas some manufacturers use mixtures of these materials, a common combination being clay and titanium dioxide or clay and calcium carbonate. During the manufacture of paper, it is important to control the ash content of the paper. The concentration of ash can affect the strength of the paper and also certain qualities such as printability. Furthermore, clay, which is often a component of ash, is generally far cheaper than wood fiber. Therefore, it is often important to maintain the ash content as high as reasonably possible while still maintaining other characteristics of the paper within specification.

On a related aspect of papermaking, it is often desirable to coat a paper sheet (called a "base sheet") with any of a wide variety of materials. Indeed, an increasing proportion of the world's paper production is devoted to coated paper and coated paperboard. Coatings are usually applied to provide a glossy white surface for magazine pages, gift wrapping, shoe boxes, and the like. Alternatively, or in addition, such coatings may also be intended to render the paper sheet waterproof.

There are a large variety of coating formulations, many of which consist of as many as ten or more components. These components can be broadly classified as pigments, binders, and additives, almost always as aqueous dispersions. Common pigments include clay, calcium carbonate, barium sulfate, and titanium dioxide. Barium sulfate and titanium dioxide are used primarily for photographic papers and specialty papers, respectively. Generally speaking, clay has been the most common pigment, although $CaCO_3$ and PCC (precipitated calcium carbonate) are becoming more common. Various formulations of latexes are commonly used for binders to hold the pigment particles together and to bond them to the paper. A typical coating formulation includes 80% to 90% pigment, 3% to 10% latex, with the remainder consisting of additives or other components.

It is often desirable to obtain measurements of selected components of sheet materials during manufacture. Various sensor systems have been developed for detecting sheet properties "on-line," i.e., on a sheet-making machine while it is operating. Typically, on-line sensor devices are operated to periodically traverse, or "scan," traveling webs of sheet material during manufacture. Scanning usually is done in the cross direction, i.e., in the direction perpendicular to the direction of sheet travel. Unfortunately, obtaining an accurate cross-direction, i.e., cross-web, or machine-direction profile of a minor individual component or additive, such as $CaCO_3$ or latex which are used as ash or coating component, is typically not feasible with conventional techniques such as x-ray, infrared absorption or x-ray fluorescence. For example, fluorescing dyes are of limited use because of low signal to noise ratios, low photostability, and lack of sensitivity. In particular, many fluorescing dyes have broad emission spectra and narrow absorption spectra thereby limiting the number of components that can be detected. In addition, it is difficult to discriminate the fluorescence associated with a particular dye given the high background and the broad emission spectra of the various dyes. Further, in the case of $CaCO_3$, when the component is present in both the base sheet and the coating, two separate sensors are needed to perform the measurements. Finally, specialty paper makers often include components that do not exhibit unique signatures and therefore are not readily detectable by conventional techniques.

SUMMARY OF THE INVENTION

The present invention is based in part on the recognition that incorporating fluorescent nanoparticles such as quantum dots, with their unique optical emissions properties, into paper and other web products such as plastics enables cross-direction and machine direction on-line detection of selected components during manufacture. Specifically, fluorescent nanoparticles markers or tags are added in known proportions into product formulations along with the selected components of interest. By detecting the fluorescence from the nanoparticles, the selected components can be traced at various stages of production. Moreover, by employing different species of fluorescent nanoparticles that emit radiation at different wavelengths, data from individual materials or layers in a composite structure can be ascertained simultaneously with a single sensor. Fluorescent nanoparticles which are inorganic materials offer substantial advantages over organic dyes, including a longer half-life, a broad excitation spectrum, a narrow, symmetric emission spectrum, and minimal photobleaching. In particular, in a multi-component system that uses three or more species of fluorescent nanoparticles as markers for four or more corresponding selected components, the advantages of fluorescent nanoparticles such as quantum dots are even more evident. Specifically, each species of fluorescent nanoparticles exhibits emission spectrum that is sufficiently narrow and tunable, that multiple colors of quantum dots can be discerned. In contrast, it is difficult to detect more than three dyes and the photo-bleaching effects make quantitative measurements less reliable and accurate. Finally, the fluorescent properties of many organic dies are temperature dependant, that is, their fluorescence is often reduced at elevated temperatures.

The present invention is particularly suited for monitoring expensive and difficult-to-measure components that may be present only in trace quantities. While the technique can be implemented continuously during normal production, it can be used during start-up or re-formulation, such as a grade change in paper production, when considerable changes in the process parameters occur.

Accordingly, in one aspect, the invention is directed to an on-line method of monitoring the presence of at least one selected component in a traveling web composition that includes the steps of:

(a) forming an initial web composition at a first location that comprises at least one selected component and at least one species of fluorescent nanoparticles, wherein the amount of the least one species of fluorescent nanoparticles relative to the amount of the at least one selected component is known;

(b) exposing the web composition to a light source that causes the at least one species of fluorescent nanoparticles to emit fluorescent light;

(c) measuring fluorescent light that is emitted by the at least one species of fluorescent nanoparticles in the web composition at a second location that is downstream from the first location; and (d) correlating the fluorescent light measurements made in step (c) to levels of the at least one selected components in the web composition.

In another aspect, the invention is directed to a method of monitoring the production of paper material in a papermaking machine from wet stock wherein a sheet of wet stock is initially developed on a water permeable moving wire of a forming section of a de-watering machine and thereafter a sheet of partially de-watered web stock is transferred to a dry end section of the de-watering machine, which method includes the steps of:

(a) forming wet stock comprising fibers and at least one selected component and at least one species of fluorescent nanoparticles at a first location that is on the water permeable moving wire, wherein the amount of the at least one species of fluorescent nanoparticles relative to the amount of the at least one selected component is known;

(b) operating the papermaking machine so that a traveling sheet of material develops and moves downstream in a machine direction through the papermaking machine such that the sheet of material is subjected to a plurality of operations that transform the wet stock into paper;

(c) exposing the at least one species of fluorescent nanoparticles to a light source that causes the at least one species of fluorescent nanoparticles to emit fluorescent light; and (d) measuring the fluorescent light that is emitted by the at least one species of the fluorescent nanoparticles in the traveling sheet of material at a second location that is downstream from the first location.

BRIEF DESCRIPTION OF THE DRAWINGS

FIG. 1 shows a sheetmaking system implementing the technique of the present invention;

FIG. 2 shows the development of a sheet of wet stock on the wire of the sheetmaking system;

FIG. 3 is a cross-sectional view of a multiply board; and

FIG. 4 is a cross-sectional view of a coated sheet.

DETAILED DESCRIPTION OF PREFERRED EMBODIMENTS

FIG. 1 shows a papermaking system for producing continuous sheet material that comprises headbox 2, a calendaring stack 10, and reel 8. Actuators 32 in headbox 2 discharge raw material through a plurality of slices onto supporting wire 24 which rotates between rollers 12 and 16. Foils and vacuum boxes (not shown) remove water, commonly known as "white water," from the wet stock on the wire into the wire pit 18 for recycle. A dry line 42 of demarcation forms on the wire which corresponds to the point where a glassy layer of water is no longer present on the top of the stock. Sheet material exiting the wire passes through a dryer 4. A scanning sensor, that includes an optical source 6 and an optical detector 36, which is supported on supporting frame 22, continuously traverses the sheet and measures properties of finished sheet 20 in the cross-direction. Multiple stationary sensors could also be used. Scanning sensors are known in the art and are described, for example, in U.S. Pat. No. 5,094,535 to Dahlquist et al., U.S. Pat. No. 4,879,471 to Dahlquist, U.S. Pat. No. 5,315,124 to Goss et al, and U.S. Pat. No. 5,432,353 to Goss et al., which are incorporated herein by reference. The finished sheet product 20 is then collected on reel 8. As used herein, the "wet end" or "forming" portion of the system depicted in FIG. 1 includes headbox 2, wire 24, and those sections just before the dryer, and the "dry end" comprises the sections that are downstream from dryer 4.

The papermaking raw material which includes fibers is metered, diluted, mixed with any necessary additives, and finally screened and cleaned as it is introduced into headbox 2 from storage source 38 by fan or feeding pump 34. This pump mixes stock with the white water and delivers the blend to headbox 2. The process of preparing the wet stock includes the step of subjecting the fibers to mechanical action in refiner 40.

FIG. 2 illustrates headbox 2 having slices 44 which discharge wet stock 48 onto wire 24. For a headbox that is 300 inches (7.62 m) in length, there can be 100 or more slices. The rate at which wet stock is discharged through nozzle 46 of the slice can be controlled by a corresponding actuator which, for example regulates the diameter of the nozzle. The function of the headbox is to take the stock delivered by the fan pump and transform a pipeline flow into an even, rectangular discharge equal in width to the paper machine and at uniform velocity in the machine direction. Forming board 50 supports wire 24 at the points of jet impingement. The board serves to retard initial drainage.

The present invention can be employed to monitor the mass of one or more selected components that are present beginning at the initial wet stock, through partially de-watered intermediate products, and to the finished products. The process is particularly suited for monitoring the contents of important additives used in papermaking. Depending on the grade of paper being made, common non-fibrous additives include: (1) fillers such as clay (kaolin, bentonite), calcium carbonate, talc (magnesium silicate), and titanium dioxide which improve optical and surface properties, and (2) optical brighteners which improve the apparent brightness of the paper products. Synthetic polymers such as latexes and natural polymers such as starches are often admixed with the stock to improve the physical properties of the dry paper sheet.

For each additive that is to be monitored, a corresponding species of fluorescent nanoparticle is selected and included with the additive when the wet stock is formulated. The amount of the particular species of fluorescent nanoparticle relative to the amount of additive is known. In this fashion, the intensity of the emission spectra emitted by the fluorescent nanoparticle yields data that can be correlated to the additive. Typically, the fluorescent nanoparticles are metered as separate components; alternatively, the fluorescent nanoparticles can be attached to the fibers, in the case of a papermaking process, or can be attached to the non-fibrous additive(s) of interest. Regardless of the number of species of fluorescent nanoparticles used, it is preferred to limit their amounts so that the nanoparticles themselves do not adversely affect the structural integrity of the layers to which they are added. Typically, incorporating two million particles per square meter for each species of fluorescent nanoparticle is sufficient. When the layer of material is newsprint paper, this is equivalent to approximately one picogram/kg of newsprint or $10^{-14}$ g/m$^2$. In operation, with respect to a papermaking process, metered amounts of one or more species of quantum dots are mixed into the wet stock in storage source 38 (FIG. 1). The quantum dots can be in the unmodified form and/or they can be incorporated or attached to other materials as described herein. In either case, the relative amounts of the selected components being monitored and the corresponding species of fluorescent nanoparticles are known. It should be noted that in continuous papermaking processes, broke which is material taken from various locations in the machine is recycled (collected and re-pulped then fed back into the headbox). The presence of fluorescent nanoparticles in the broke must be account for in calculating the total amount that goes into the headbox.

Fluorescent nanoparticles refer, generally to semiconductive or metallic particles that exhibit fluorescence when exited by an external excitation source and that have a diameter in the range of about 1 nm to about 1000 nm, preferably in the range of about 5 nm to about 200 nm, more preferably in the range of about 10 nm to about 100 nm. Preferred fluorescent nanoparticles include three-dimensional fluorescent semiconductive nanocrystals or quantum dots which consists of crystalline semiconductors which are small enough so that electrons within suffer from quantum confinement such that the properties of the quantum dots are changed from those of bulk semiconductors. The semiconductor materials typically range in size from 1 to 100 nm. Quantum dots can be manufactured such that their optical emission peaks are very narrow. Different sizes of quantum dots will exhibit different emission spectra yet be all excitable by the same optical source which has an excitation wavelength that is lower than that of the emission peaks. Thus quantum dots of the same material but with different sizes can emit light of different colors. Surface-modified quantum dots that are water stable are described in U.S. Pat. No. 7,192,780 to Liu et al., U.S. Pat. No. 6,872,450 to Liu et al, and U.S. Pat. No. 6,649,138 to Adams et al., which are all incorporated herein by reference.

Quantum dots can also be encapsulated with polymers with specific physical properties as described in U.S. Pat. No. 7,081,489 to Chen et al., which is incorporated herein by reference. Suitable polymers are preferably a water insoluble, thermoplastics which include, but are not limited to, polyamides, polycarbonates, polyalkenes, polyvinyl ethers, polyglycolides, cellulose ethers, (e.g., hydroxy propyl cellulose, hydroxy propyl methyl cellulose, and hydroxy butyl cellulose), polyvinyl halides, polyglycolic acid, and polylactic acid. By encapsulating different species of fluorescent nanoparticles with each species being shielded with a polymer shell with a known melting point, a distribution of different species of fluorescent nanoparticles with coatings that melt at different temperatures is obtained. Such a distribution of fluorescent nanoparticles can be used, for instance, to determine the temperature range within a calendar stack by monitoring the emission spectra at the calendar stack.

Polymeric nanocoatings have been developed which have the capacity to spectrally shift the emission spectrum in response to changes in pH. See "Design of pH Sensors in Long-Period Fiber Gratings Using Polymeric Nanocoatings," J. Corres et al. IEEE Sensors Journal, 7 (3), 455, 2007. These nanofilm coatings are formed by electrostatic self-assembly of multilayer films of poly(acrylic acid) and poly-(allylamine hydrochloride). Certain characteristics of the coatings such as their thicknesses are influenced by the pH in the environment where they are exposed. Changes in the thickness in turn affect their optical properties. pH sensitive coated fluorescent nanoparticles could be used to monitor the pH on the wet end of the papermaking machine.

Bifunctional surface modifiers can be used to link quantum dots to ash particle (TiO$_2$) surfaces. See "Assembly of CdS quantum dots onto mesoscopic TiO2 films for quantum dot-sensitized solar cell applications," Yu-Jen Shen and Yuh-Lang Lee, 2008 Nanotechnology (19) 045602. Different species of quantum dots can thus be attached to corresponding ash particles. Polymeric retention aids are employed to papermaking to improve the retention of fines at the wire. US Patent Application 2007/0258316 to Matula describes improved methods of introducing polymeric retention aids into the paper making process whereby the polymeric structure of the retention aid remains intact. US Patent Application 2007/0119561 to Doelle et al. describes a method of loading cellulose fibers with calcium carbonate; the so-treated fibers are capable of retaining much higher levels of ash. Thus, another technique of incorporating fluorescent nanoparticles to components of the wet stock is to first attach quantum dots to polymeric retention aids. It is believed that these modified polymers will adhere to treated and non-treated cellulose fibers.

Fluorescent nanoparticles can also be attached to larger components in the various formulations in which the present invention is applied. For instance, in the case of wet stock that forms paper fluorescent nanoparticles can be attached to cellulose fibers to yield tagged-fibers. An advantage of being attached to fibers is that the fluorescent nanoparticles are less likely to be removed in the de-watering process. Attachment can be accomplished through covalent bonding, adsorption, and physical immobilization.

Suitable quantum dots must be robust enough to withstand industrial processes where they are applied. Quantum dots are available from Evident Technologies (Troy, N.Y.) and are marketed as (i) EVICOMPOSITES which are water-stable quantum dots that would be suitable for papermaking and other aqueous applications and (ii) EVITAGS which are quantum dots that are integrated into resins and polymer matrix materials. The latter type of quantum dots can be employed in plastics applications. The quantum dots have a core of CdSe and a ZnS shell. For infrared applications they have InGaP core and a ZnS shell. Preferred quantum dots emit visible or near infrared fluorescence upon exposure to ultraviolet light illumination.

In the case where only one component within a single layer of material is to be monitored, an appropriate amount of any suitable fluorescent nanoparticle can be employed. However, if a single layer of material contains two components of interest, then two different species of fluorescent nanoparticles, which emit fluorescent light at different wavelengths, are needed. In other words, each species of fluorescent nanoparticles exhibits an emission spectrum that is different from those of the other species used in the same application. Similarly, if one component is present in two distinct layers of a multilayer structure then two species of fluorescent nanoparticles are required to monitor the presence of each component in the two layers. An example of this scenario is paper that is coated with a pigment layer and both the paper and the pigment include $TiO_2$ which is monitored. Preferably, the different species of fluorescent nanoparticles are excited by the same optical source which generates radiation with a narrow wavelength band. Alternatively, the different species can be excited by radiation having different wavelengths.

In order to use the intensity of the emission spectra of the fluorescent nanoparticles as a gauge of the mass contents of selected components, it is necessary to first calibrate the papermaking system to establish correlations between intensity measurements and the amounts of fluorescent nanoparticles. Calibration can be performed using the papermaking system under actual operating conditions or in the laboratory under simulated conditions. Calibration curves and/or mathematical relationships between emission intensity and fluorescent nanoparticle mass can be established with standard techniques. Ideally, the percentage of the selected component being monitored and the percentage of the corresponding fluorescent nanoparticle species remain constant throughout the papermaking process. This essentially means that the same percentage of the selected component and the fluorescent nanoparticles is drained from or retained in the wet stock, intermediary products and finished products. In other words, to the extent that the selected component is removed during the process, its corresponding fluorescent nanoparticle follows the same pattern and is removed at the same rate from the various stages of the process. The only practical way to insure this phenomenon is to use fluorescent nanoparticles that are attached to the component being monitored. In the case where this behavior is present, then the intensity of the emission spectrum of a species of fluorescent nanoparticle can be readily correlated to the mass of the component of interest since the relative amounts of the two were known when the wet stock was first formulated.

However, in the more prevalent situation where the selected component and the corresponding fluorescent nanoparticle do not exhibit the same behavior, tests will need to be conducted to determine their drainage or retention patterns. Given that the fluorescent nanoparticles are smaller than the typical additives used in papermaking, it is expected that fluorescent nanoparticles will be more readily removed than the additive. Once the drainage or retention patterns are determined, the differences in behavior will be taken into account when calculating the mass content of the component from the emission spectrum of the fluorescent nanoparticle.

As an example of implementing the inventive technique to measure the content of calcium carbonate in the papermaking process, a suitable species of fluorescent nanoparticle species is selected and added along with calcium carbonate to form the papermaking raw material in wet stock storage 38 of FIG. 1. The relative amounts of the species of fluorescent nanoparticle and calcium carbonate in the raw material are known. During operation of the papermaking machine, after paper 20 travels into the dry end and just after being surface-sized in calendaring stack 10, paper 20 is exposed to excitation radiation, e.g., UV illumination, from radiation source 6 which causes the fluorescent nanoparticles to emit visible or near IR light which is detected by detector 36. It is often desirable to irradiate the paper with radiation of sufficient irradiance to create a saturated population of excited quantum dots. By scanning source 6 and detector 36 back-and-forth cross the traveling paper, both cross direction and machine direction profiles of the calcium carbonate weight in the paper can be generated. If necessary, the scanner can be programmed to dwell over each target area to allow the detector to accumulate radiation counts. It is understood that measurements can be taken anywhere downstream from where wet stock 48 is discharged onto wire 24 as shown in FIG. 2.

The radiation source can comprise a quasi-broadband source such as mercury or xenon arc-discharge lamp. These sources can be appropriately filtered so the excitation spectrum does not interfere with the quantum dot emission spectrum. Detector 36 can comprise, for example, a photomultiplier tube, avalanche photodiodes or electron multiplying charge-coupled device. If two or more species of fluorescent nanoparticles are employed in the wet stock so that a corresponding number of different emission spectra are emitted, detector 36 is equipped with beam splitters to split incident radiation into two or more beams of radiation that are directed to individual optical filter/detector units. Each unit measures the intensity of one of the emission spectra. Suitable radiation sources and detectors can be configured and implemented as shown in U.S. Pat. No. 5,795,394 to Belotserkovsky et al., which is incorporated herein by reference.

As is apparent, the inventive technique is most suited when the radiation emitted from the fluorescent nanoparticles is readily transmitted through the material into which the fluorescent nanoparticles are incorporated. In the case where fluorescent nanoparticles are part of in a thin optically transparent coating that is applied to a substrate, the transmission losses are small and essentially all of the radiation can be detected. However, in the case where the fluorescent nanoparticles are incorporated into an interior layer of a multilayer structure, then attenuation of the emitted radiation is likely and this phenomenon must be accounted for. One method of compensating for this is to recognize that longer wavelength radiation travel farther than shorter wavelength radiation, thus, fluorescent nanoparticles that emit radiation with longer wavelengths should be used in the interior layers.

The CD and MD weight profiles generated by the inventive process can be employed to control the papermaking process in order to produce paper with the desired calcium carbonate distribution. Techniques for controlling sheetmaking machines are described in U.S. Pat. No. 6,466,839 to Heaven et al., U.S. Pat. No. 6,092,003 to Hagart-Alexander et al., and U.S. Pat. No. 6,086,716 to Watson et al., which are all incorporated herein by reference.

Another embodiment of the inventive process provides on-line measurements of one or more components in multilayer structures. FIG. 3 depicts a cross section of a multiply board which is produced by the consolidation of two or more web plies into a single sheet of paperboard. This seven ply board includes a top liner 26, underliner 28 and bottom liner 30. The other four layers are filler plies which can be made from inexpensive and bulky low-grade waste materials. Multiply paperboard machines are described in U.S. Pat. No. 4,376,012 to Bergstrom and U.S. Pat. No. 4,239,593 to Dunsmoor, which are incorporated herein by reference.

During the manufactured of each of the individual plies, one or more species of fluorescent nanoparticles can be incorporated in the ply in known proportions relative to the selected components of interest. The inventive process can be employed for on-line measurements of the selected components. Moreover, during assembly of the multiply from the individual plies in a multiply paperboard machine, the inventive technique can be employed to monitor the selected components as well.

A further embodiment of the inventive process provides on-line measurements of one or more components in coated paper. Techniques for coating paper sheets are described in U.S. Pat. No. 7,255,918 to Watanabe et al. and U.S. Pat. No. 6,074,483 to Belotserkovsky et al., which are incorporated herein by reference. FIG. 4 shows base sheet 54 that has an upper coating 52 and lower coating 56. Selected components in any or all three layers can be measured by incorporating appropriate species of fluorescent nanoparticles and detecting their emission spectra.

For example, in the production of high gloss paper, a thin coating 52 containing $CaCO_3$ is applied to a base sheet 54 which may include $CaCO_3$ as well. The invention provides an on-line non-contact method of simultaneously measuring the amount of $CaCO_3$ that is present in the gloss coating and in the base sheet. In particular, when wet stock is formulated with a known amount of $CaCO_3$, a predetermined amount of a first species of fluorescent nanoparticle also is incorporated. Thus, the base sheet paper that is made will have both $CaCO_3$ and the first species homogeneously incorporated therein. Similarly, when the gloss formulation is prepared with a known amount of $CaCO_3$, a predetermined amount of a second species of fluorescent nanoparticle is also added. Preferably, both species of fluorescent nanoparticles are excited by the same optical source which generates radiation with a narrow wavelength band, and the first species emits radiation having a longer wavelength than that emitted by the second species. As the homogeneously mixed gloss coating is applied onto the base sheet, a scanning source and detector located downstream travel back-and-forth cross the traveling paper to measure the intensities of the fluorescent light that are emitted by the first and second species. In this fashion, both cross direction and machine direction profiles of the calcium carbonate weight in the paper and coating can be generated.

The foregoing has described the principles, preferred embodiments and modes of operation of the present invention. However, the invention should not be construed as being limited to the particular embodiments discussed. Thus, the above-described embodiments should considered as illustrative rather than restrictive, and it should be appreciated that variations may be made in those embodiments by workers skilled in the art without departing from the scope of the present invention as defined by the following claims.

What is claimed is:

1. An on-line method of monitoring the presence of at least one selected component in a traveling web composition that comprises the steps of:
   (a) forming an initial web composition at a first location that comprises at least one selected component and at least one species of fluorescent nanoparticles, wherein the amount of the least one species of fluorescent nanoparticles relative to the amount of the at least one selected component is known wherein the at least one selected component is not attached to the at least one species of fluorescent nanoparticles;
   (b) exposing the web composition to a light source that causes the at least one species of fluorescent nanoparticles to emit fluorescent light;
   (c) measuring fluorescent light that is emitted by the at least one species of fluorescent nanoparticles in the web composition at a second location that is downstream from the first location; and
   (d) correlating the fluorescent light measurements made in step (c) to concentrations of the at least one selected components in the web composition wherein the at least one selected component exhibits drainage patterns that are different from those of the at least one species of fluorescent nanoparticles and step (d) applies this difference in correlating the fluorescent light measurements to the concentrations of the at least one selected components.

2. The method of claim 1 wherein step (b) comprises exposing the web composition to radiation having a first wavelength and detecting radiation having a second wavelength that is emitted by the at least one species of fluorescent nanoparticles.

3. The method of claim 1 wherein step (a) comprises forming an initial web composition that comprises a multilayer web comprising at least two layers and wherein at least two layers of the multilayer web have a selected component and a corresponding species of fluorescent nanoparticle therein.

4. The method of claim 3 wherein a first selected component is present in both a first layer and a second layer of the initial multilayer web, wherein the first layer includes a first species of fluorescent nanoparticle and the second layer includes a second species of fluorescent nanoparticle.

5. The method of claim 4 wherein step (b) comprises exposing the web composition to radiation including wavelengths in at least a first and a second separate wavelength regions and measuring radiation that is emitted by the first species of fluorescent nanoparticles and the second species of fluorescent nanoparticles.

6. The method of claim 4 wherein the multilayer web comprises paper that is coated with a pigment layer.

7. The method of claim 4 wherein the pigment layer includes pigment that is selected from the group consisting of titanium dioxide, calcium carbonate, clay, latex, starch, a brightener, and mixtures thereof.

8. The method of claim 3 wherein the multilayer web comprises a substrate with a coated-layer thereon.

9. The method of claim 1 wherein the initial web composition comprises a substrate that is coated with at least one layer of material and wherein at least one of the layers comprises at least one selected component and at least one species of fluorescent nanoparticles.

10. The method of claim 9 wherein the substrate also comprises at least one selected component and at least one species of fluorescent nanoparticles.

11. The method of claim 1 wherein step (a) comprises forming an initial web composition that travels along in a machine direction and step (b) comprises obtaining radiation measurements at multiple locations in the machine direction, in a cross direction, or in both in directions.

12. The method of claim 1 wherein step (d) comprises comparing the fluorescent light measurements to calibration profiles that correlate the fluorescent measurements to amount of the at least one selected component in the web composition.

13. The method of claim 1 wherein the at least one species of fluorescent nanoparticles is coated with a shielding material that degrades at a predetermined temperature.

14. An on-line method of monitoring the presence of at least one selected component in a traveling web composition that comprises the steps of:
   (a) forming an initial web composition at a first location that travels along in a machine direction and that comprises at least one selected component and at least one species of fluorescent nanoparticles, wherein the amount of the least one species of fluorescent nanoparticles relative to the amount of the at least one selected component is known wherein the at least one species of fluorescent nanoparticles is attached to cellulose fibers in the web composition, wherein the at least one selected component is not attached to the at least one species of fluorescent nanoparticles, and wherein the at least one selected component exhibits drainage patterns that are different from those of the at least one species of fluorescent nanoparticles;

(b) exposing the web composition to a light source that causes the at least one species of fluorescent nanoparticles to emit fluorescent light;

(c) measuring fluorescent light that is emitted by the at least one species of fluorescent nanoparticles in the web composition at a second location at multiple locations in a cross direction (CD) that is downstream from the first location;

(d) correlating the fluorescent light measurements made in step (c) to concentrations of the at least one selected components in the web composition to generate a CD profile; and (e) employing the CD profile to control step (a) to produce an initial web composition with the desired distribution of the at least one selected component along the CD.

15. An on-line method of monitoring the production of paper material in a papermaking machine from wet stock wherein a sheet of wet stock is initially developed on a water permeable moving wire of a forming section of a de-watering machine and thereafter a sheet of partially de-watered web stock is transferred to a dry end section of the de-watering machine, which method comprises the steps of:

(a) forming wet stock comprising fibers and at least one selected component and at least one species of fluorescent nanoparticles at a first location that is on the water permeable moving wire, wherein the amount of the at least one species of fluorescent nanoparticles relative to the amount of the at least one selected component is known and wherein the at least one selected component exhibits a drainage pattern through the water permeable moving wire that is different from that of the at least one species of fluorescent nanoparticles;

(b) operating the papermaking machine so that a traveling sheet of material develops and moves downstream in a machine direction through the papermaking machine such that the sheet of material is subjected to a plurality of operations that transform the wet stock into paper;

(c) exposing the at least one species of fluorescent nanoparticles to a light source that causes the at least one species of fluorescent nanoparticles to emit fluorescent light;

(d) measuring the fluorescent light that is emitted by the at least one species of the fluorescent nanoparticles in the traveling sheet of material at a second location that is downstream from the first location; and (e) correlating the fluorescent measurements made in step (d) to concentrations of the at least one selected components in the traveling sheet.

16. The method of claim 15 further comprising the steps of: (i) coating the traveling sheet with a coating layer of material that includes at least one selected component and at least one species of fluorescent nanoparticles that is different from the species of fluorescent nanoparticles in the traveling sheet, and (ii) exposing of the coating layer to a light source that causes the species of fluorescent nanoparticles to emit fluorescent light, (iii) measuring the fluorescent light that is emitted by the species of the fluorescent nanoparticles in the traveling sheet, the coating layer or in both the traveling sheet and the coating layer and (iv) correlating the fluorescent light measurements in step (iii) to concentrations of the at least one selected components in the traveling sheet, coating layer or both traveling sheet and coating layer.

17. The method of claim 15 wherein step (b) comprises obtaining radiation measurements at multiple locations in the machine direction, in a cross direction, or in both directions.

18. The method of claim 15 wherein the at least one species of fluorescent nanoparticles is attached to the fibers.

19. The method of claim 15 wherein the at least one selected component is selected from the group consisting of titanium dioxide, calcium carbonate, clay, latex, starch, a brightener, and mixtures thereof.

20. The method of claim 15 wherein the at least one selected component is not attached to the at least one species of fluorescent nanoparticles.

* * * * *